United States Patent [19]

He et al.

[11] Patent Number: 5,532,492

[45] Date of Patent: Jul. 2, 1996

[54] NUCLEAR GAUGE WITH COMPENSATION FOR SAMPLE IRREGULARITIES

[75] Inventors: Tianqing He; Ali Regimand, both of Raleigh, N.C.

[73] Assignee: Troxler Electronic Laboratories, Inc., Research Triangle Park, N.C.

[21] Appl. No.: 321,546

[22] Filed: Oct. 12, 1994

[51] Int. Cl.[6] .................................................. G01N 23/09
[52] U.S. Cl. ............................. 250/390.05; 250/390.04; 250/391
[58] Field of Search ...................... 250/390.04, 390.05, 250/391, 392

[56] References Cited

U.S. PATENT DOCUMENTS

| | | |
|---|---|---|
| 3,492,479 | 1/1970 | Lowery et al. . |
| 3,532,883 | 10/1970 | Dresia et al. . |
| 3,761,712 | 9/1973 | Listerman ...................... 250/390.05 X |
| 4,499,380 | 2/1985 | Aggour et al. ...................... 250/390.04 |
| 4,645,635 | 2/1987 | Yuen et al. ...................... 250/390.05 X |
| 4,874,950 | 10/1989 | Regimand ...................... 250/390.05 X |
| 4,884,288 | 11/1989 | Sowerby . |
| 5,083,029 | 1/1992 | Buchanan ........................... 250/390.05 |
| 5,151,601 | 9/1992 | Regimand . |

FOREIGN PATENT DOCUMENTS

| | | | |
|---|---|---|---|
| 1155924 | 10/1963 | Germany ........................... 250/390.05 |
| 53-86300 | 7/1978 | Japan ................................ 250/390.05 |

Primary Examiner—Carolyn E. Fields
Assistant Examiner—Edward J. Glick
Attorney, Agent, or Firm—Bell, Seltzer, Park & Gibson

[57] ABSTRACT

A neutron gauge is described for determining the moisture content of a moisture containing material. Samples of the moisture containing material are confined in a sample pan and a sample cover with sufficient neutron moderating activity is pressed against the sample. The cover, sample, and sample pan are placed in the same location in the gauge with respect to the neutron source and detector for each measurement to compensate for volume variations in the sample. The sample can be weighed to compensate for density variations. The sample pan cover can include a cadmium sheet for direct contact with the sample to shield the sample from neutrons thermalized by the cover.

33 Claims, 4 Drawing Sheets fig. 1.

NUCLEAR GAUGE WITH COMPENSATION FOR SAMPLE IRREGULARITIES

FIELD OF THE INVENTION

The invention relates to nuclear gauges and to methods based on neutron thermalization theory for determining the hydrogen content of hydrogen-containing materials and for determining characteristics of various materials based on their hydrogen content.

BACKGROUND OF THE INVENTION

Mass produced paper and some similar textile products typically are prepared from a stock that is a dilute suspension of fibers in water of a specified low concentration. The concentration of fibers in suspension is often referred to as the "consistency" of the stock. Controlling the consistency of the stock through the pulping, pulp bleaching, and paper making processes is important for maintaining control over these processes. The consistency of the paper stock directly affects the efficiency of each of the processes.

Typically, the consistency of the stock varies from about 3 to 30 percent in the pulping and bleaching processes. Current pulping and bleaching processes are usually accomplished at a consistency of from about 10 to 15 percent. Stock consistency for paper making operations varies from about 0.5 to 5 percent.

Online devices are available for determining the consistency of dilute paper stock at consistencies of about 5 percent or less. Online devices are expensive and typically only one location on the process line is chosen for online determination of stock consistency. Online devices usually do not provide sufficiently accurate results at consistencies above about 5 percent. Laboratory methods are used for spot checking, trouble shooting, and for determination of stock consistency at consistencies above about 5 percent.

One laboratory method in general use is based on the gravimetric principle and is subject to large sampling error. This method is time consuming, prone to human and instrument errors, and examines a relatively small sample of 10 to 30 grams compared to a much larger heterogeneous volume of stock that is actually used in the pulping, pulp bleaching, and paper making processes.

Paper stock typically has the appearance of a thick slurry of fibers in water at consistencies above about 5 percent. Samples usually vary significantly in density and in volume. Previous attempts to use portable nuclear gauges to determine the moisture content of paper stock and other materials having variation in sample volume and density generally have not provided consistent results. The gauges are sensitive to volume changes in materials.

Compensation for measuring uncertainty in the use of portable nuclear gauges typically has been accomplished by attempting to maintain consistent compaction and surface conditions for successive measurements of the sample to reduce variations in density and volume. However, consistent conditions are difficult and time consuming to maintain in practice.

SUMMARY OF THE INVENTION

The invention claimed herein is based upon the recognition that surface characteristics and compaction can vary for each sample for many materials, including soil, industrial raw materials including paper stock and wood chips, agricultural products including corn and other grains, and various construction materials including gravel and coarse asphalt mixes. The materials listed above typically are presented as relatively thick suspensions of solids in liquids or as loose collections of individual coarse pellets having variations in dimension, shape, rigidity, and porosity. Changes in surface conditions and compaction can result in changes in sample volume and density for each sample.

When subjected to fast neutrons, the neutron energy spectrum in the sample does not reach an equilibrium condition in which the overall profile of the neutron energy spectrum remains relatively constant at successively varied sample volume. The non-equilibrium condition of the neutron energy spectrum in the sample typically causes the gauge reading to be sensitive to volume changes in the material, which are related to changes in the surface characteristics of the samples. The relative sample volume may be small in comparison to the variations in properties of the material from which the sample is taken, which can reduce the accuracy of the volume and density determinations still further.

In accordance with the present invention a neutron moderator is provided for reducing the energy level of fast neutrons from a fast neutron source in the neutron gauge before the neutrons reach the sample. The incident neutrons in the sample therefore have a higher proportion of slower neutrons above a specified energy level than neutrons directly penetrating the sample from the fast neutron source with no reduction in the energy level before entering the sample. An equilibrium condition in the sample is approached and the gauge sensitivity to volume changes is reduced.

In accordance with one aspect of the invention, there is provided an apparatus for determining the hydrogen content of a hydrogen-containing material. The apparatus comprises a neutron gauge housing having a sample chamber therein adapted for receiving a sample so that the hydrogen content thereof can be measured. A sample is positioned in the sample chamber. A source of fast neutrons is provided in the housing on one side of the chamber for subjecting the sample to neutron radiation. A neutron moderator is positioned between the source and the sample and is positioned relative to the sample so as to substantially preclude fast neutrons from reaching the sample while permitting moderated neutrons to reach the sample. A detector is provided in the housing for detecting thermalized neutrons. The detector is located opposite the neutron moderator from said neutron source. A means for calculating the hydrogen content of the sample cooperates with the detecting means to calculate hydrogen content from the thus detected thermalized neutrons.

In one embodiment, the neutron moderating substance is of the same dimensions as a conventional sample pan and is designed to fit into the sample pan as a cover on top of the sample that is received in the sample pan and in direct contact with the surface of the sample. The sample pan is provided with tabs to secure the cover in place and to prevent the cover from lifting off the sample.

The cover can be a block of a fixed quantity of polyethylene of predetermined thickness. In another embodiment the cover can be a block of polyethylene or other suitable neutron moderating substance and includes a material that is opaque to thermal neutrons, sometimes called a "black material" for thermal neutrons, for absorbing thermal neutrons interposed between the neutron moderator and the sample. The cover should be placed in the sample pan with a layer of material containing boron or cadmium in direct contact with the sample.

For example, a polyethylene block can have a boron or cadmium sheet attached thereto for absorbing neutrons that are thermalized by the polyethylene block and other materials within the sample chamber. The material for absorbing thermal neutrons shields the sample from thermal neutrons and substantially precludes thermal neutrons from entering the sample. Thermal neutrons entering the sample add a high background to the gauge counts and reduce the ratio of the thermal neutrons scattered in the sample to those scattered outside the sample, resulting in a reduction of the signal to noise ratio.

In yet another aspect of the present invention, there is provided a method for determining the hydrogen content of a hydrogen-containing material. The method comprises subjecting a sample of a hydrogen-containing material to a fast neutron source, reducing the energy level of fast neutrons from the source prior to entry into the sample, detecting neutrons that have been thermalized by the sample, and then determining the hydrogen content of the sample based upon the thus detected thermalized neutrons.

In one embodiment of the method, the step of reducing the energy level of fast neutrons from the source prior to entry into the sample comprises interposing between the neutron source and the sample a neutron moderator that covers the surface of the sample that faces the neutron source.

In a more specific embodiment of the method, the step is included of determining the moisture content of a moisture-containing material. Additional steps include calibrating the gauge to determine the moisture content of the sample from a count of thermalized neutrons that result from the sample, obtaining the weight of the sample, confining the sample in a sample pan, selecting a block of polyethylene of predetermined thickness from a set of blocks of various thicknesses depending upon the neutron moderating activity of the sample, covering the sample in the sample pan with the block in direct contact with the sample, subjecting the sample to neutrons from a fast neutron source, taking a count of thermalized neutrons, and determining the moisture content per unit weight of the sample in accordance with the predetermined calibration curve from the thus obtained count of thermalized neutrons and the weight of the sample.

Thus, the invention provides, among other things, a portable nuclear gauge that can be used quickly and accurately to determine the consistency of paper stock and the moisture content of a variety of materials in the laboratory. Relatively large volumes of sample can be examined at a time with measuring certainty, up to at least about 500 grams.

BRIEF DESCRIPTION OF THE DRAWINGS

Some of the features and advantages of the invention have been stated. Other features and advantages will become apparent as the description proceeds taken in connection with the accompanying drawings, in which.

DETAILED DESCRIPTION OF THE INVENTION

The invention will now be described more fully with reference to the drawings and in connection with a particular neutron gauge designed for measuring the moisture content of paper stock. The invention can, however, be used to measure other properties that can be correlated with the hydrogen content of a sample material and can be used with other types of neutron gauges. For example, the invention can be used to determine the amount of moisture in industrial raw materials, construction materials, and agricultural products including among them wood chips, soil, gravel, corn and other grains, and others to numerous to mention. The invention is particularly useful for determining the moisture content of materials such as paper stock having a large liquid component and for determining the moisture content of materials that are a loose collection of individual coarse pellets having fairly large variations in pellet dimension, shape, rigidity, and porosity.

Although the invention is intended for use with materials that have nonuniform density or rough surfaces, the invention can be used to determine characteristics correlated with hydrogen content for samples of material that are relatively uniform in density and surface characteristics. It should be understood therefore that the specific embodiments described herein are illustrative of how the present invention may be practiced, and that the invention is not limited to these specific embodiments.

Figure 1:
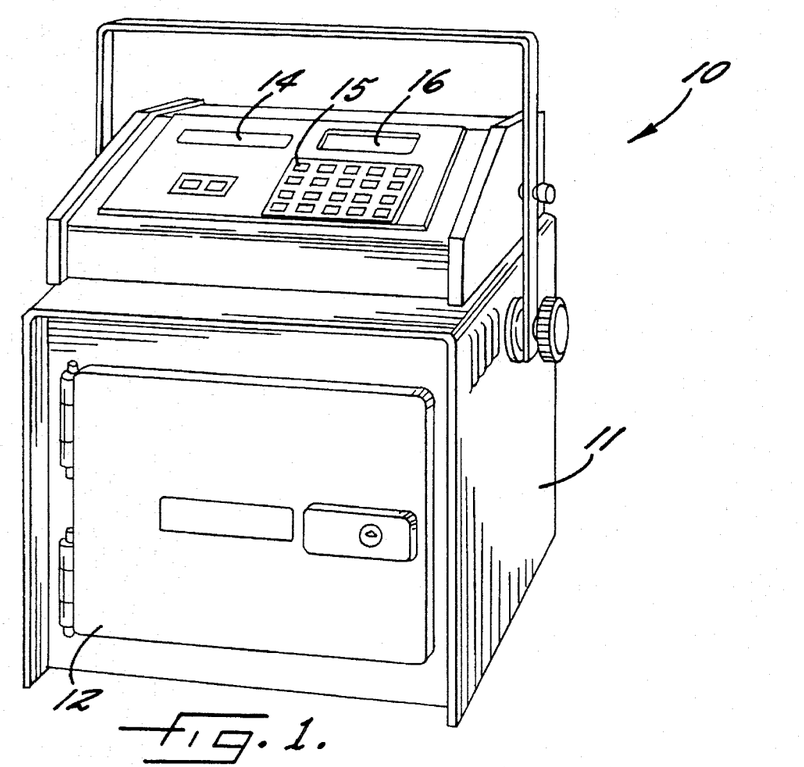
FIG. 1 is a perspective view of a neutron gauge.

A neutron gauge is generally indicated by the number 10 in FIG. 1 and comprises a generally rectangular housing 11 having a door 12 that provides access to a measurement chamber in which sample pans are placed for measurement. A control unit 14 is provided, including a keypad 15 for entry of data and for controlling the functions of the gauge and a display 16, which may be of any suitable construction, such as a liquid crystal display.

Figure 2:
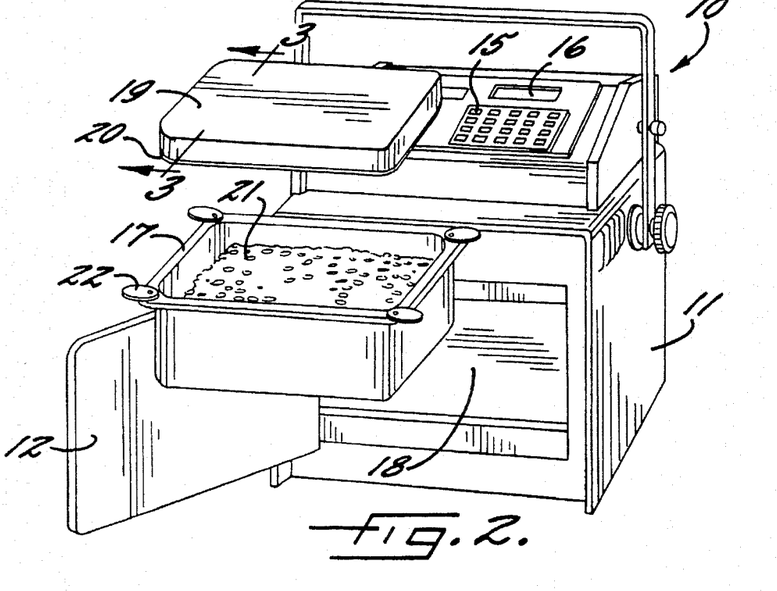
FIG. 2 is an exploded perspective view of the neutron gauge of FIG. 1, showing a sample tray, a polyethylene cover block having a cadmium sheet attached thereto, and a sample of a moisture containing material in accordance with the present invention.

Referring to FIG. 2, there is shown an exploded view of the components of the invention. A sample pan 17 is sized to fit into the measuring chamber or sample receiving cavity 18 of the neutron gauge. Samples that have a liquid component or are a loose collection of pellets should be confined in a suitable container such as sample pan 17. Samples of uniform dimension may not need to be confined in a sample pan so long as the samples can be located in the same position in the gauge for successive measurements.

A cover comprising a polyethylene block 19 having a cadmium sheet 20 fixed thereto is shown disposed above the sample pan and is sized to be closely fitted within the sample pan on top of a sample 21 and to cover the sample. The cover and its components are shown in longitudinal cross section in FIG. 3. Swivel tabs 22 are provided on the sample pan for securing the cover in place so that the cover does not lift off the surface of the sample and remains fixed in contact with the sample during measurement. It should be recognized that other suitable means for securing the cover in contact with the sample could be used.

Polyethylene contains a fixed amount of hydrogen in its molecular structure. It effectively serves as a neutron moderating substance and reduces the energy level of fast neutrons prior to entry of the neutrons into the sample from a neutron source. In addition, polyethylene is relatively inert and its hydrophobic property renders it relatively unaffected by changes in ambient moisture and substantially precludes its absorbing moisture from a material whose moisture content is to be measured.

However, it should be appreciated that other materials may be used to reduce the energy of fast neutrons, so long as the material does not chemically react with the sample material, does not absorb or release moisture, and provides a means for reducing the energy level of the fast neutrons prior to entry into the sample. For example, a water filled hollow polyethylene article or block or a metal block filled with a neutron moderating material should be suitable.

It is desirable to include a material that absorbs thermal neutrons with the block of material for reducing background counts in detectors. Some of the neutrons passing through the block of neutron moderating material will become thermalized and will be counted by the detector if these neutrons enter the sample. These thermal neutrons will add a large background count in measurement and reduce the signal to noise ratio.

Figure 3:
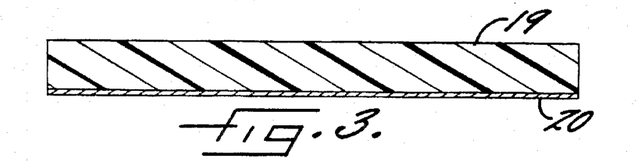
FIG. 3 is a longitudinal cross sectional view of the polyethylene block and Cadmium sheet combination of FIG. 2 taken along line 3—3 in accordance with the present invention.

Accordingly, it is useful to place a material that is opaque to thermal neutrons between the neutron moderating block and the sample to absorb neutrons that have been thermalized by the neutron moderating material. Such materials sometimes are said to be "black" materials for thermal neutrons. In the illustrated embodiment, for example, the material for absorbing thermal neutrons is a cadmium sheet 20. Cadmium effectively shields the sample from thermal neutrons. It should be appreciated, however, that other materials may also be used to absorb thermal neutrons so long as the material does not chemically react with the sample material, does not absorb or release moisture, and absorbs thermal neutrons. For example, a boron sheet should be suitable.

In the embodiment illustrated herein, the cover, comprising the polyethylene block 19, which is of about ½ inch thickness, and the cadmium sheet 20, which is of about 0.018 inches thickness, is shown for placement by pressing in direct contact with the sample with the cadmium sheet interposed between the sample and the polyethylene block. It has been determined that somewhat more accurate results can be obtained when the cover is in close contact with the sample, thus increasing the flux, or intensity, of slower neutrons that enter the sample and interact with the sample. Fewer interactions are required for the sample to thermalize a neutron to a detectable level, and the number of effective interactions to thermalize a neutron is increased. In the case of measurement of porous materials, such as in determination of pulp consistency, the cover also serves as a tool to confine the material to a predetermined level inside the sample pan, so that a substantially consistent packing condition can be achieved for each measurement.

To obtain the most accurate and reproducible results, it is important that the energy reducing means be positioned in a fixed or consistent location in relation to the source and detector. In the illustrated embodiment, the block is shown located in the sample pan on top of the sample and fixed by swivel tabs and the pan is designed to be received in the same location within the sample receiving cavity of the gauge housing. Accordingly, consistent positional relationship is achieved.

However, it should be understood that the neutron moderator could be provided at other locations within the gauge than that location that is illustrated, while still reaping the benefits of the invention. For example, the neutron moderator could be placed in any fixed location between the neutron source in the gauge and the surface of the sample facing the neutron source, so long as the energy reducing means covers the surface of the sample that faces the neutron source. A desirable geometry for neutron transmission through the sample places the sample between the source, which is at the top of the typical gauge, and the detector, which is typically below the sample. If desired, the sample pan could be lifted by conventional mechanical means or designed so that the sample pan could be precisely located in the gauge housing with respect to a cover. Although somewhat less practical, the neutron moderator could be located on the bottom of the sample pan or below the sample pan and above the source if the neutron source were located on the bottom of the gauge.

Figure 4A:
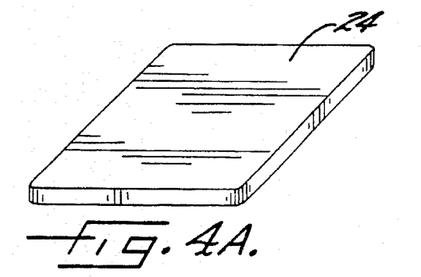
FIGS. 4A, 4B, and 4C illustrate various thicknesses of polyethylene blocks for use in accordance with the present invention.
Figure 4B:
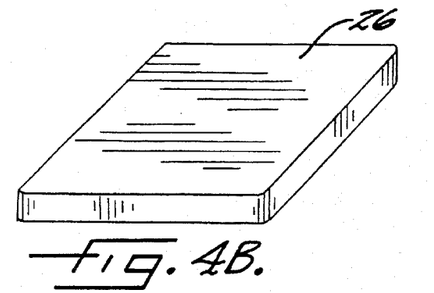
Figure 4C:
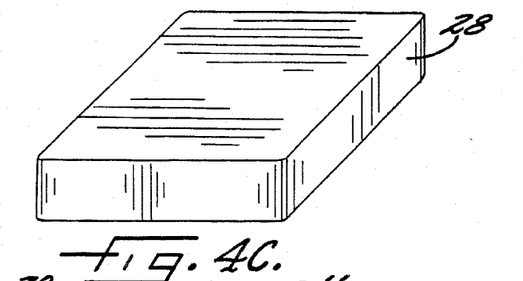

Various thicknesses of polyethylene blocks for use in connection with the invention as sample pan covers are shown in FIGS. 4A, 4B, and 4C in the absence of opaque materials for thermalized neutrons. The degree of neutron moderating activity of a polyethylene block and most other neutron moderating materials typically varies in direct proportion to the thickness of the material. More accurate results can be obtained using the apparatus of the invention if the thickness of the neutron moderating material is correlated with the nature of the sample to optimize the geometry for transmission of slow neutrons above a specified energy level through the sample.

For example, a ½ inch thick polyethylene block has been determined to be useful for determining the uniformity and consistency of paper stock. A ⅛ inch block has been determined to be useful for determining the asphalt content of a coarse bituminous paving mix. The appropriate thickness of the particular neutron moderating material is determinable empirically without undue experimentation based on comparison with materials of known hydrogen content or of a known characteristic that is directly correlated to hydrogen content, such as moisture content in the case of paper stock or asphalt content in the case of bituminous paving mixes.

Figure 5:
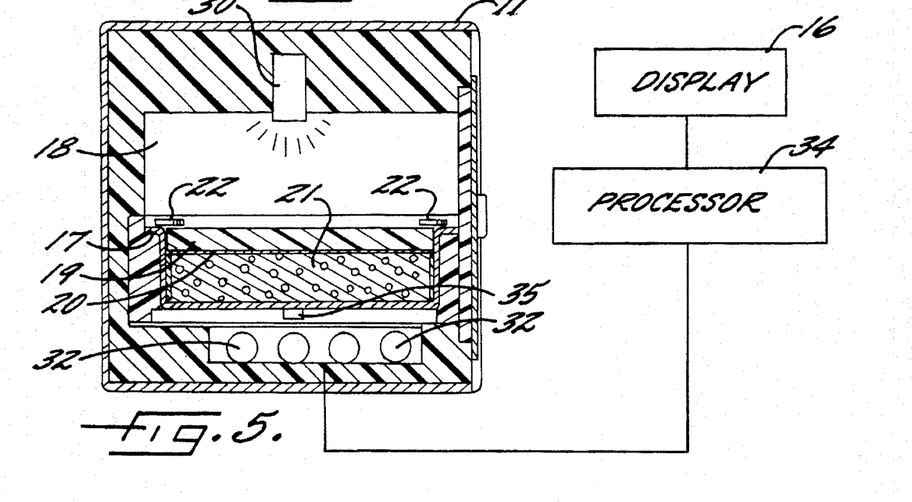
FIG. 5 is a cross sectional view of the neutron gauge of FIG. 1 having placed therein a sample tray, a cover having a polyethylene block with a cadmium sheet attached thereto, and a sample of a moisture containing material in accordance with the present invention.

Referring to FIG. 5, measurement chamber 18 receives sample pan 17, sample 21, and the sample cover comprising polyethylene block 19 and cadmium sheet 20. Located in the upper interior portion of the gauge is a source 30 of fast neutrons. The source 30 may, for example, suitably comprise a Californium 252 source, an Am-241:Be source, or others that should be apparent to the skilled artisan. In the lower interior portion of the gauge beneath the sample pan are a series of detector tubes 32 for detecting neutrons that have been slowed or thermalized by interaction with hydrogen atoms present in the sample. The illustrated detectors 32 are $He^3$ detector tubes, but any suitable thermal neutron detector will suffice. The gauge also includes a processor module 34 for controlling the gauge, counting thermalized neutrons, and determining the moisture content from a previously established correlation.

It should be recognized that the detector tubes can be placed in other locations than that illustrated, depending on the location of the source and the sample. For example, the detector tubes for the illustrated embodiment could be located on the interior side portions of the gauge housing with the detector tubes on the opposite side of the neutron moderator from the source. The detector tubes should be placed so that the detector tubes do not extend into the plane in which the neutron moderator is located or onto the side of the neutron moderator on which the source is located.

The weight of the sample can be obtained using a suitable conventional scale outside the apparatus. Alternatively, an electronic scale, such as a load cell 35, which is based on electrical resistance measurement, can be incorporated in the gauge housing to weigh the sample, sample pan, and cover and to convey a signal to the processor to which is applied a correction factor to calculate the sample weight. In either case, the data can be entered into processor module 34 by an electrical signal or by an operator.

To operate the gauge, the paper stock sample 21 is confined in the sample pan 17. The polyethylene and cadmium sheet cover is pressed on top of the sample with the cadmium sheet 20 in direct contact with the surface of the sample and swivel tabs 22 are turned to secure the cover on top of the sample and in contact with the sample. If no scale is included in the gauge housing, then the weight of the sample is determined. The sample pan with the sample and cover is inserted into the interior of the gauge. The sample pan, the sample, and the cover are weighed if the scale includes suitable weighing means. The weight is entered into processor module 34 and a correction factor is applied to subtract out the weight of the sample pan and cover. The door is shut and fast neutrons from the source 30 are emitted down through the polyethylene cover 19, the cadmium sheet 20, the sample of paper stock 21, and the sample pan 17 to the detectors 32.

Fast neutrons from the source interact with hydrogen nuclei present in the polyethylene block of the cover. The hydrogen nuclei in the cover modify the energy level of the fast neutrons down to a low energy level. Thermal neutrons that are thermalized by the polyethylene block are absorbed by the cadmium sheet and are substantially precluded from entering the sample. Low energy neutrons enter the sample and interact with hydrogen nuclei present in the sample. Detector tubes 32 detect the thermalized neutrons below a specified energy level.

The thermal neutrons are counted for a predetermined period and a count is recorded in the data processor module 34. The processor module 34 then correlates the number of counts and the weight of the sample to a moisture content by using a previously established calibration curve and indicates the result in display 16 for the paper stock being tested, if desired.

It should also be recognized that the moisture content of the sample can be determined with respect to unit volume of the sample. The counts and volume can be correlated with a previously established calibration curve based on counts per unit volume and the results indicated, if desired.

Figure 6:
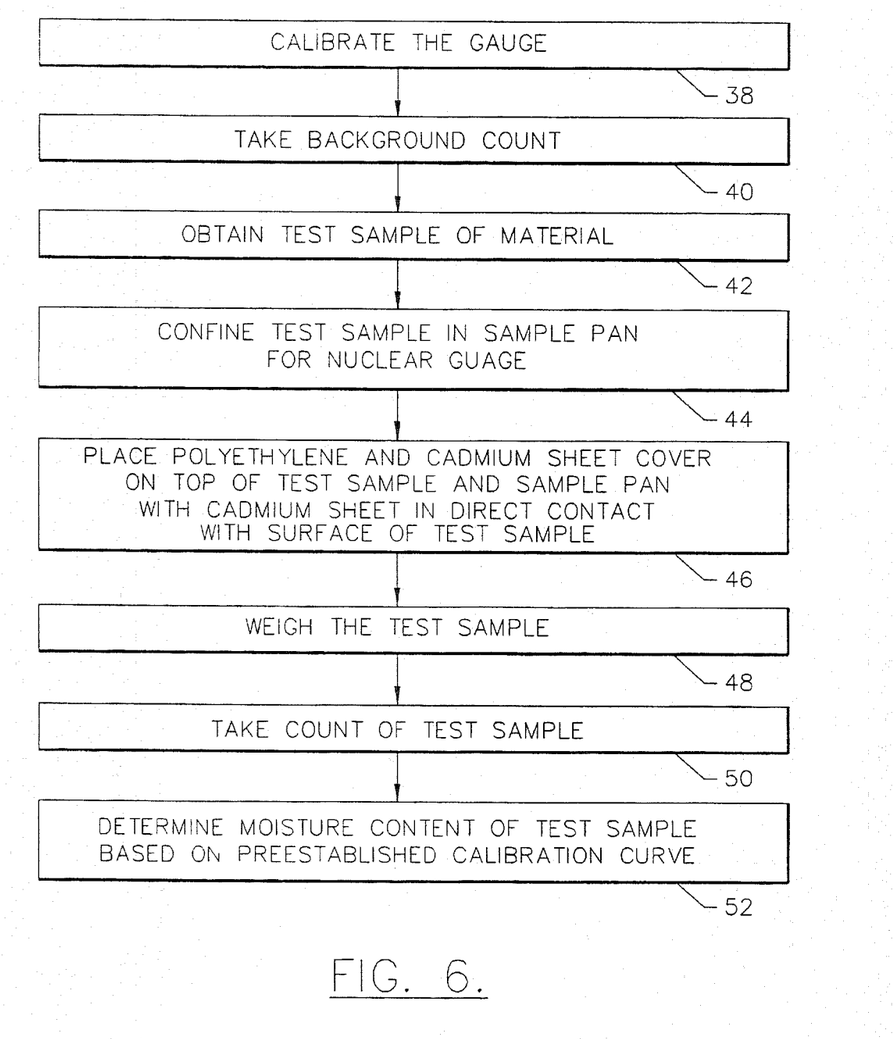
FIG. 6 is a flow chart illustrating the basic procedures followed according to one embodiment of the invention.

The basic procedure for determining the moisture content of a test sample of paper stock is described with reference to the flow diagram in FIG. 6. It is first necessary to calibrate the gauge in accordance with step 38. The procedure for calibrating the neutron gauge to determine the moisture content of paper stock is described with reference to FIG. 7.

An initial background count will have been taken when the gauge is calibrated. However, the background count of thermalized neutrons will change with the location of the gauge. It is recommended that the background count be determined on a daily basis in accordance with step 40. Changes in the background count from that established when the gauge was calibrated can then be taken into account in calculating the moisture content of test samples.

Test samples of unknown moisture content are obtained and confined in sample pans. As illustrated in steps 42 through 52, these samples are obtained, placed in a sample pan, covered with the polyethylene and cadmium sheet cover, weighed, and the counts of the test samples are then taken and the moisture content of the samples determined. In accordance with step 52, the moisture content of the test samples is determined from the counts and weight of the test samples in accordance with the preestablished calibration.

Figure 7:
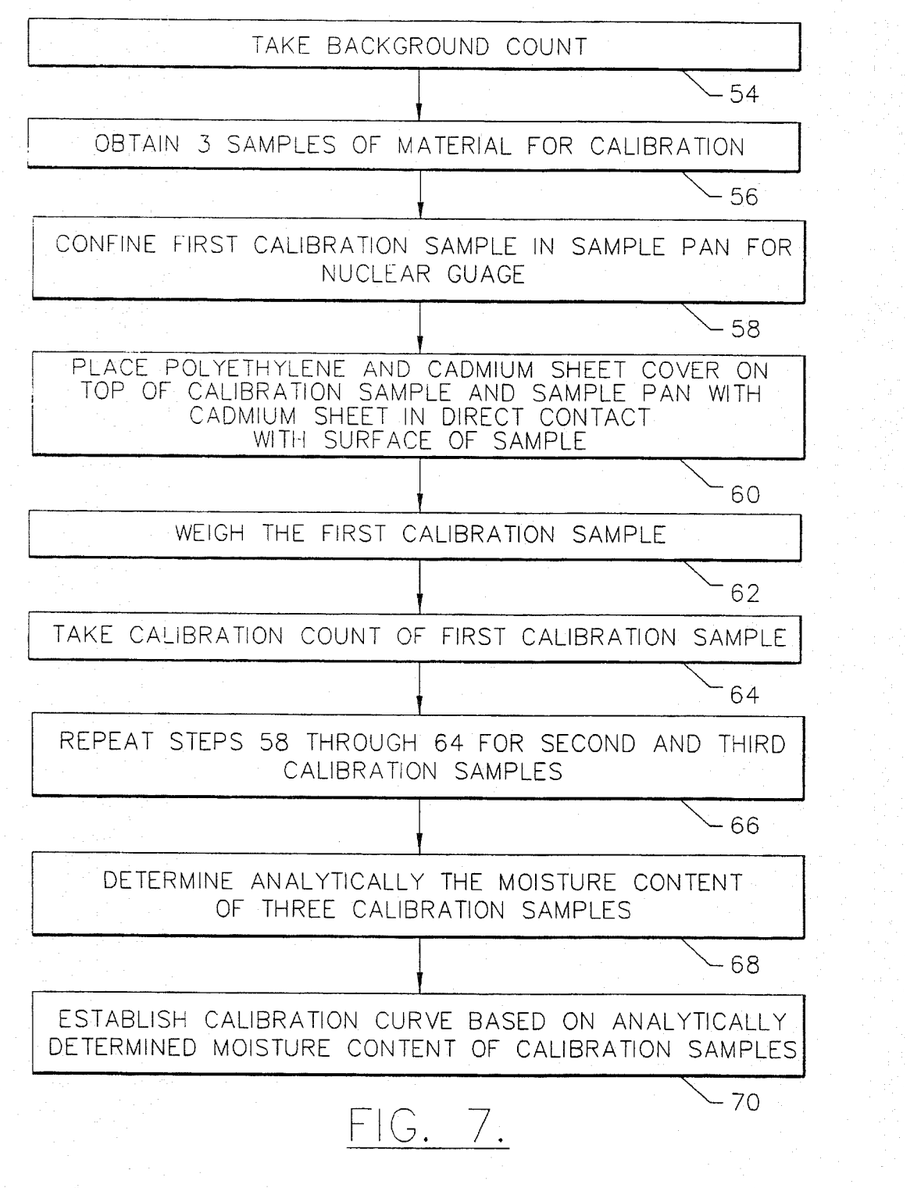
FIG. 7 is a flow chart illustrating detailed procedures for calibrating a neutron gauge in one embodiment of the invention.

With reference to FIG. 7, the first step in calibrating the gauge, which is illustrated at 54, is to take a background count of thermalized neutrons. Once the background count is determined, measurements of neutron moderating activity are made on each of two or more samples, each of which has a slightly different moisture content, for calibration of the apparatus. Generally speaking, at least two samples of different percent moisture should be analyzed for use in establishing a calibration curve. However, it is preferred analytically to establish the moisture content of three or more samples. These three samples can be used, for example, to establish the norm and the upper and lower limits for moisture content for test samples of unknown moisture content. For example, counts may be taken for three different samples, one having a moisture content of 10 percent, one of 13 percent, and one of 15 percent, or other suitable levels, to establish the desired moisture level in the paper stock and upper and lower limits for acceptable moisture content.

As indicated in step 56, three samples of paper stock are obtained for calibration. The samples are confined in a conventional sample pan for the neutron gauge and placed in the neutron gauge with the polyethylene and cadmium sheet cover in place as described above, all in accordance with steps 58 and 60. The samples are weighed as in step 62. The samples are subjected to a neutron source. Thermalized neutrons are detected and counted for each calibration sample in accordance with steps 64 and 66.

To complete the process of calibrating the gauge, the thermalized neutron count and sample weight for each sample is correlated with the moisture content of the sample. Accordingly, once the background count and the counts for the calibration samples are obtained, then the next step 68 is to determine analytically the moisture content of the calibration samples. Typically, the moisture content of these calibration samples is determined by weighing a sample of the paper stock, removing all of the water content from the paper stock by heating the paper stock to drive off the moisture, and then weighing the bone dry paper stock to determine the weight loss due to the moisture content.

The moisture content of the calibration sample is determined analytically after the count of thermalized neutrons is taken. No moisture is removed from the calibration samples until after the counts are taken. This method of calibrating the neutron gauge has the advantage that the same samples are used for the thermalized neutron count as for analytic determination of moisture content. Accuracy of measurement of test samples is provided based on the calibration curve that is established from the calibration counts per gram of sample and the analytically determined moisture content.

The calibration curve is established in accordance with step 70 based on the analytically determined moisture content of the calibration samples and the counts obtained for them. The counts obtained for the samples can be fitted to a polynomial or any suitable equation. The parameters for the calibration equation are stored in processor 34, which is illustrated in FIG. 5, and these parameters are thereafter used to determine the moisture content of unknown test samples. In this manner, the gauge is calibrated to determine the moisture content of unknown test samples having a cover placed thereon for reducing the energy level of fast neutrons prior to entry into the sample of the neutrons from the source.

What is claimed is:

1. Apparatus for determining the hydrogen content of a hydrogen-containing material comprising, in combination:

a gauge housing having a sample chamber therein adapted for receiving a sample so that the hydrogen content thereof can be measured, a sample positioned in said sample chamber, a fast neutron source provided in the housing on one side of said chamber for subjecting said sample to neutrons, a neutron moderator positioned between said source and said sample, said neutron moderator being so positioned relative to said sample as substantially to preclude fast neutrons from reaching said sample from said source while permitting moderated neutrons to reach said sample, a detector for detecting thermalized neutrons, said detector provided in the housing opposite the neutron moderator from said neutron source, and means cooperating with said detector for calculating from the thus detected thermalized neutrons the hydrogen content of said sample.

2. An apparatus according to claim 1 wherein said neutron moderator covers the surface of said sample that faces said neutron source.

3. An apparatus according to claim 2 wherein said neutron moderator is in contact with the surface of said sample.

4. An apparatus according to claim 1 wherein said neutron moderator is in the shape of a block and is of a thickness sufficient to reduce the energy level of the fast neutrons to a substantially lower energy level above thermal equilibrium.

5. An apparatus according to claim 1 wherein said neutron moderator comprises polyethylene.

6. An apparatus according to claim 1 wherein said apparatus further comprises means for shielding said sample from thermal neutrons.

7. An apparatus according to claim 6 wherein said thermal neutron shielding means comprises a material selected from the group consisting of cadmium and boron.

8. An apparatus according to claim 6 wherein said thermal neutron shielding means is interposed between said sample and said neutron moderator.

9. An apparatus according to claim 1 further comprising:

means for calculating the moisture content of said sample from the calculated hydrogen content, means for weighing said sample, and means for calculating the moisture content per unit weight of said sample, said means cooperating with said weighing means and said means for calculating the moisture content of said sample.

10. An apparatus for determining the moisture content per unit weight of a moisture-containing sample of material, said apparatus comprising, in combination:

a gauge housing having a sample receiving cavity therein, a sample pan adapted to be positioned in the sample receiving cavity of the housing with a sample confined therein, a cover for said sample pan comprising a neutron moderator of predetermined thickness, a neutron source provided in the housing on the same side of said sample pan as said cover, and a thermalized neutron detector provided in the housing on the opposite side of said sample pan cover from said neutron source.

11. An apparatus according to claim 10 further comprising:

means for determining the weight of the sample in the sample pan, and means cooperating with said detector means and said weighing means for calculating from the thus detected thermalized neutrons and the thus determined weight of a sample the moisture content per unit weight of the sample.

12. An apparatus according to claim 10 wherein said cover comprises a polyethylene block sized to fit as a cover on said sample pan.

13. An apparatus according to claim 10 further comprising a sheet of material that absorbs thermal neutrons interposed between the cover and the surface of the sample and in contact with the surface of the sample on one side thereof and with the cover on the other side thereof.

14. An apparatus according to claim 13 wherein the sheet of material is selected from the group consisting of cadmium and boron.

15. An apparatus for determining the moisture content per unit weight of samples of material, said apparatus comprising, in combination:

a gauge housing having a sample receiving cavity and a door that provides access to said cavity, a control unit for the gauge housing including a keypad for entry of data and for controlling the functions of the gauge and a display for displaying measurements obtained by the gauge, a sample pan for confining therein a sample and sized to closely fit into the sample receiving cavity, a cover for the sample in the sample pan, said cover comprising a polyethylene block of predetermined thickness having a cadmium sheet fixed thereto, said cover being sized to extend completely over the surface of the sample confined in the sample pan with the cadmium sheet in contact with the surface of the sample, a neutron source provided in the housing on one side of said cavity for subjecting to neutrons through said polyethylene block and cadmium sheet the sample confined in the sample pan and covered by said polyethylene block and cadmium sheet, detector tubes provided in the housing on a side of said cavity opposite said sample cover for detecting neutrons thermalized by the neutron moderating characteristics of the sample, and a processor cooperating with the detector tubes for calculating from the detected thermalized neutrons the moisture content of the sample.

16. An apparatus according to claim 15 further comprising means for determining the weight of the sample in said sample pan, said means cooperating with said processor for calculating the moisture content per unit weight of the sample.

17. An apparatus according to claim 15 further comprising means located on said sample pan for securing said cover in contact with the sample.

18. A method for determining the hydrogen content of a sample of a hydrogen-containing material, comprising:
   a) confining the sample in a sample chamber of an instrument that houses a fast neutron source for determining the hydrogen content of the sample;
   b) subjecting the sample in the chamber to the neutron source within the instrument;
   c) reducing the energy level of fast neutrons from the source prior to entry into the sample;
   d) detecting neutrons that have been thermalized by the sample; and
   e) determining the hydrogen content of the sample based upon the thus detected thermalized neutrons.

19. A method according to claim 18 wherein the step of reducing the energy level of the fast neutrons prior to entry into the sample of neutrons from the source comprises interposing an auxiliary neutron moderating substance between the neutron source and the sample that covers the surface of the sample that faces the neutron source.

20. A method according to claim 19 wherein the neutron moderating substance is in the form of a block and said method further comprises the steps of determining the thickness of the block needed for accurate measurement of neutron moderating activity of the sample and selecting a block of predetermined thickness for covering the sample from a set of blocks of different thicknesses.

21. A method according to claim 20 further comprising the step of positioning the neutron moderating substance in contact with the surface of the sample while subjecting the sample to a fast neutron source.

22. A method according to claim 21 further comprising the step of placing the sample in a pan having an open top and wherein the step of contacting the neutron moderating substance with the surface of the sample while subjecting the sample to a fast neutron source comprises positioning the neutron moderating substance in the pan in contact with the surface of the sample and interposed between the neutron source and the sample.

23. A method according to claim 18 further comprising the steps of determining the moisture content of the sample from the hydrogen content determined in step (d) and weighing the sample.

24. A method according to claim 23 wherein the step of weighing the sample is performed within the instrument.

25. A method according to claim 18 further comprising the step of shielding the sample from thermal neutrons.

26. A method according to claim 25 wherein the step of reducing the energy level of the fast neutrons prior to entry into the sample of neutrons from the source comprises interposing an auxiliary neutron moderating substance in the shape of a block between the neutron source and the sample that extends completely over the surface of the sample that faces the neutron source, and wherein the step of shielding the sample from thermal neutrons comprises interposing a substance that absorbs thermal neutrons between the neutron moderating substance and the sample that extends completely over the surface of the sample.

27. A method according to claim 26 wherein the substance that absorbs thermal neutrons contacts the sample on one side thereof and contacts the neutron moderating substance on the other side thereof.

28. A method for determining the moisture content of a sample of a moisture-containing material, comprising:
   a) providing a neutron gauge having a sample pan;
   b) confining a sample of a moisture-containing material in the sample pan in the neutron gauge;
   c) selecting a block of polyethylene of predetermined thickness depending upon the neutron moderating activity of the sample and the size of the sample pan;
   d) covering the sample in the sample pan with the block in contact with the sample to reduce the energy level of fast neutrons prior to entry into the sample;
   e) subjecting the sample to a fast neutron source;
   f) obtaining a count of neutrons thermalized by the sample; and
   g) determining the moisture content of the sample from the thus obtained count of thermalized neutrons.

29. A method according to claim 28 wherein the polyethylene block has a thermal neutron absorbing sheet attached thereto and said step of covering the sample in the sample pan comprises positioning the polyethylene block and attached sheet with the sheet in contact with the sample.

30. A method according to claim 28 further comprising the step of calibrating the neutron gauge to determine the moisture content of the sample, said calibrating step comprising the steps of:
   a) placing a sample in the sample pan in the gauge with the polyethylene block covering the surface of the sample in the pan;
   b) subjecting the sample to a source of fast neutrons in the gauge through the polyethylene block;
   c) detecting neutrons thermalized by hydrogen present in the sample and storing this count;
   d) determining analytically the moisture content of the sample;
   e) repeating steps (a) through (d) for at least one additional sample of different moisture content; and
   f) establishing a calibration curve based on the neutron counts detected and the analytically determined moisture content for each sample.

31. A method for determining the moisture content per unit weight of a sample of paper stock, said method comprising:
   a) obtaining a sample of paper stock;
   b) confining the sample of paper stock in a sample pan;
   c) determining the weight of the sample;
   d) subjecting the sample to a fast neutron source;
   e) reducing the energy level of fast neutrons from the source prior to entry into the sample;
   f) detecting neutrons that have been thermalized by the sample;
   g) determining the moisture content of the sample based upon the thus detected thermalized neutrons; and
   h) determining the moisture content per unit weight of the sample.

32. A method for determining the hydrogen content of a sample of a hydrogen-containing material, comprising:
   a) placing the sample in a housing of an instrument that houses a fast neutron source for determining the hydrogen content of the sample;
   b) subjecting the sample to the neutron source within the instrument housing;
   c) reducing the energy level of fast neutrons from the source prior to entry into the sample;
   d) detecting neutrons that have been thermalized by the sample;

e) determining the hydrogen content of the sample based upon the thus detected thermalized neutrons;
f) determining the moisture content of the sample from the hydrogen content determined in step (e); and
g) weighing the sample within the housing.

33. A method according to claim 32 further comprising the step of determining the moisture content per unit weight of the sample.

* * * * *